(12) United States Patent
Bünger et al.

(10) Patent No.: US 6,602,514 B1
(45) Date of Patent: Aug. 5, 2003

(54) USE OF ECTOINE OR ECTOINE DERIVATIVES IN COSMETIC FORMULATIONS

(75) Inventors: Joachim Bünger, Gross-Umstadt (DE); Hans-Jürgen Driller, Gross-Umstadt (DE); Roland Martin, Weinheim (DE)

(73) Assignee: Merck Patent GmbH, Darmstadt (DE)

( * ) Notice: Subject to any disclaimer, the term of this patent is extended or adjusted under 35 U.S.C. 154(b) by 0 days.

(21) Appl. No.: 09/744,945

(22) PCT Filed: Jul. 22, 1999

(86) PCT No.: PCT/EP99/05239

§ 371 (c)(1),
(2), (4) Date: Jan. 31, 2001

(87) PCT Pub. No.: WO00/07560

PCT Pub. Date: Feb. 17, 2000

(30) Foreign Application Priority Data

Aug. 1, 1998 (DE) .......................................... 198 34 817
Mar. 17, 1999 (DE) .......................................... 199 11 775

(51) Int. Cl.$^7$ ............................ A61K 7/42; A61K 7/44; A61K 7/021; A61K 7/025; A61K 7/06
(52) U.S. Cl. ........................... 424/401; 424/59; 424/60; 424/63; 424/64; 424/70.7; 424/70.9; 424/400; 424/401; 514/398; 514/399; 514/844; 514/937
(58) Field of Search ................................ 424/400, 401, 424/59, 60, 63, 64, 70.7, 70.9; 514/398, 399, 844, 937

(56) References Cited

U.S. PATENT DOCUMENTS 6,060,071 A * 5/2000 Motitschke et al. ........ 424/401
6,267,973 B1 * 7/2001 Motitschke et al. ........ 424/401

FOREIGN PATENT DOCUMENTS

DE     43 42 560     6/1995
EP     0 671 161 A1 *     9/1995

OTHER PUBLICATIONS

J. Bunger: Parfumerie und Kosmetik, vol. 79, No. 11, 1998, pp. 34–35.

* cited by examiner

*Primary Examiner*—Jose' G. Dees
*Assistant Examiner*—Marina Lamm
(74) *Attorney, Agent, or Firm*—Millen, White, Zelano & Branigan, P.C.

(57) ABSTRACT

The use of one or more compounds chosen from the compounds of the formulae Ia and Ib

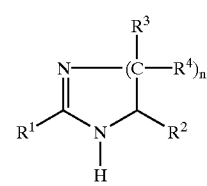

Ia

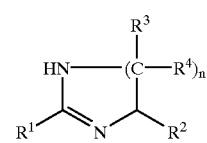

Ib the physiologically compatible salts of the compounds of the formulae Ia and Ib and the stereoisomeric forms of the compounds of the formulae Ia and Ib, where $R^1$, $R^2$, $R^3$, $R^4$ and n have the meanings given in claim 1, for the preparation of a cosmetic formulation is advantageously suitable, e.g., for protecting cells, proteins and/or biomembranes of the human skin, for protecting the microflora of the human skin, and/or for stabilizing the skin barrier.

7 Claims, 4 Drawing Sheets

Figure 1:
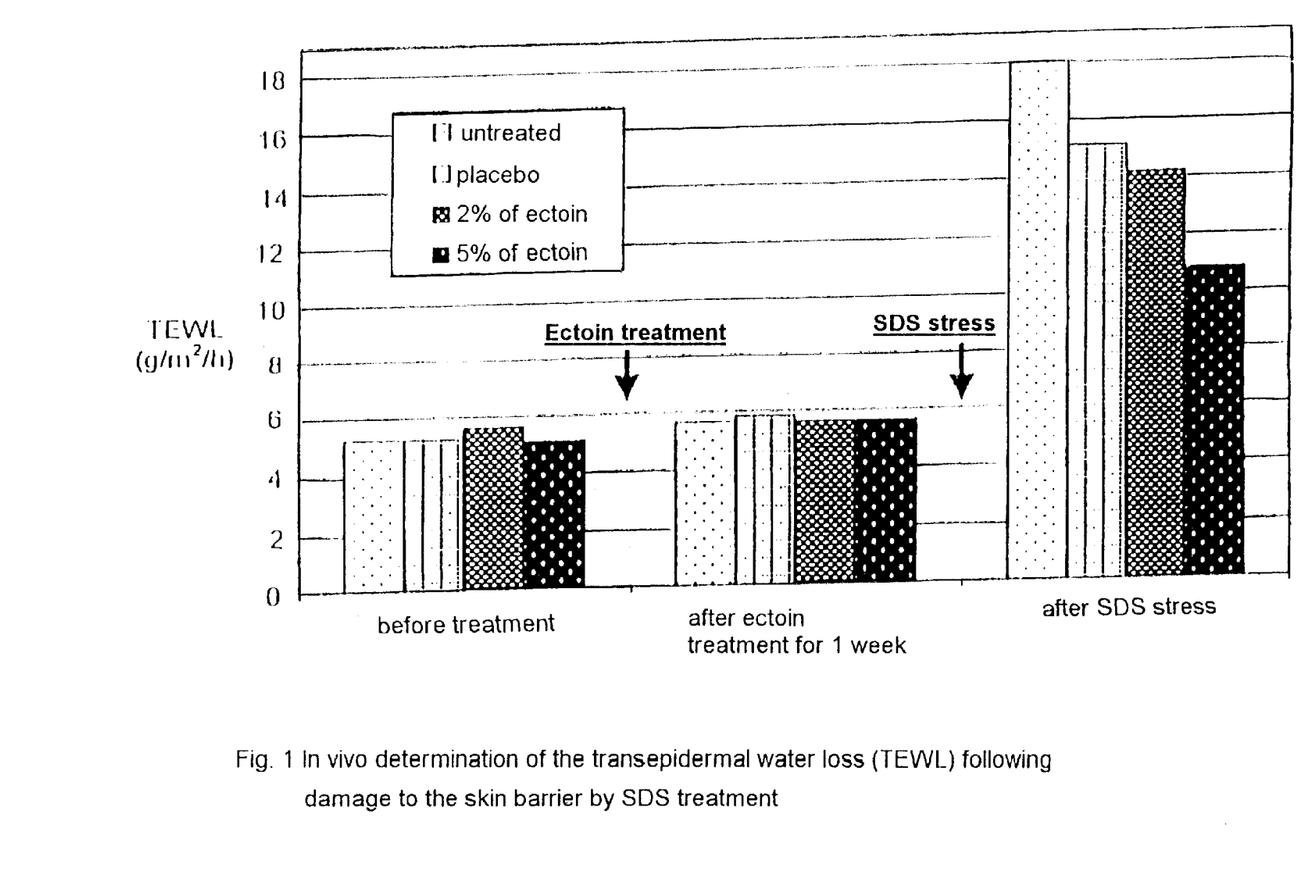
Figure 2:
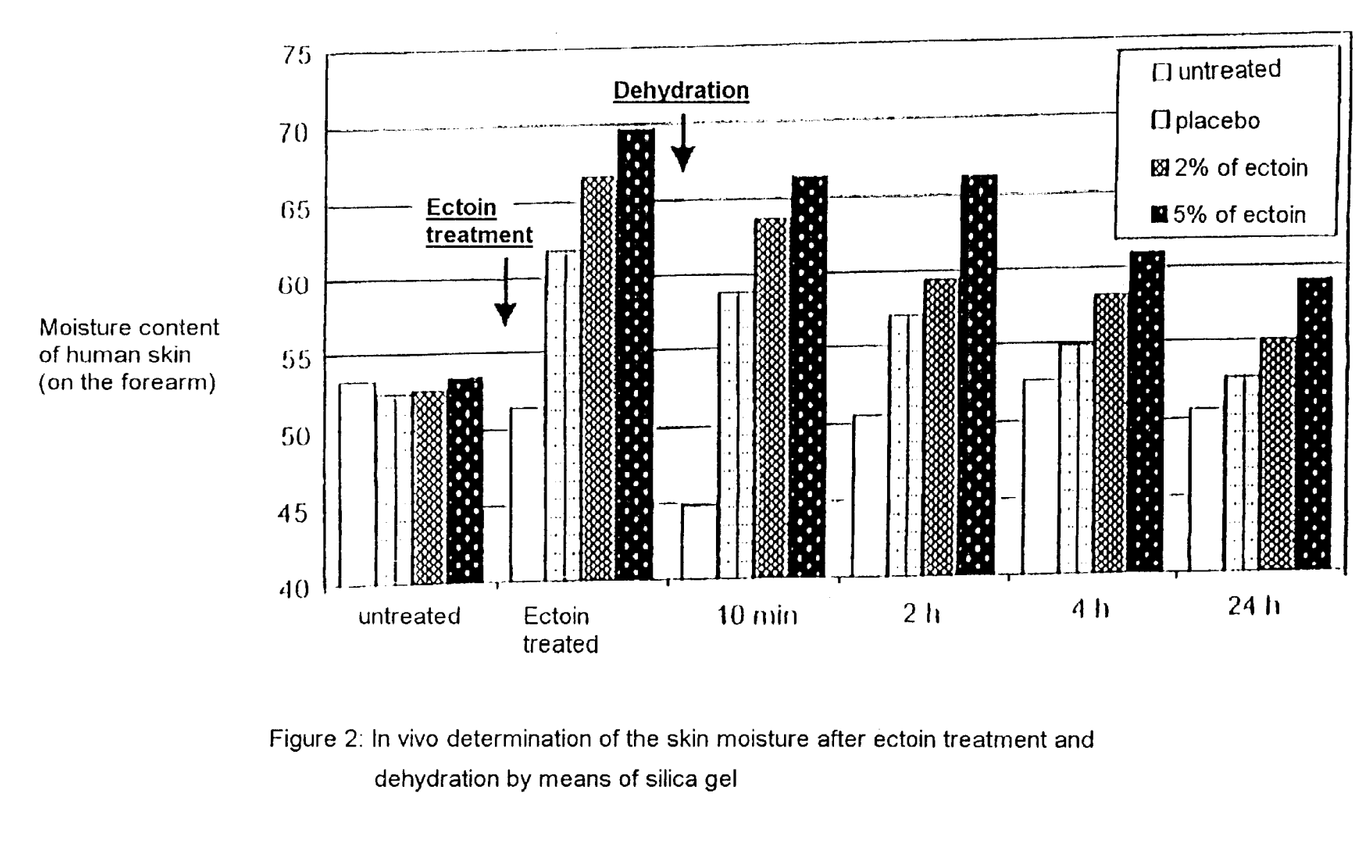

Fig. 1 In vivo determination of the transepidermal water loss (TEWL) following damage to the skin barrier by SDS treatment Figure 2: In vivo determination of the skin moisture after ectoin treatment and dehydration by means of silica gel Fig. 3 Determination of the membrane-stabilizing action of human erythrocytes pretreated with ectoin against SDS Fig. 4 Determination of the membrane-stabilizing action of human erythrocytes pretreated with ectoin against SDS

USE OF ECTOINE OR ECTOINE DERIVATIVES IN COSMETIC FORMULATIONS

The invention relates to the use of one or more compounds chosen from compounds of the formulae Ia and Ib the physiologically compatible salts of the compounds of the stereoisomeric forms of the compounds of the formulae Ia and Ib, where $R^1$ is H or alkyl, $R^2$ is H, COOH, COO-alkyl or CO—NH—$R^5$, $R^3$ and $R^4$ are in each case independently of one another H or OH, n is 1, 2 or 3, alkyl is an alkyl radical having 1 to 4 carbon atoms, and $R^5$ is H, alkyl, an amino acid radical, dipeptide radical or tripeptide radical for the preparation of a cosmetic formulation for protecting human skin from stress factors, in particular from dryness as a result of high temperatures or very low temperatures with low atmospheric humidity and/or from high salt concentration on the skin, for protecting cells, proteins and/or biomembranes of human skin, for protecting the microflora of human skin and/or for stabilizing the skin barrier.

Healthy human skin is colonized on its surface, the Stratum corneum, by a large number of microorganisms which live commensally. From the great diversity of these microorganisms, only a few live continually on the skin and thus form the resident skin flora. The main representatives of the resident flora on the human skin are Staphylococci, Micrococci, coryneform bacteria and Pityrospora. These live in small colonies on the surface of the Stratum corneum and in the outer epidermis. A second group of microorganisms, which settles temporarily from the outside, in particular on exposed areas of skin, is referred to as transient flora and cannot settle permanently on healthy skin whose microenvironment is heavily determined by the resident microflora. In various regions of the body, the composition of the skin flora varies depending on the microenvironment of the skin. The density of the microorganisms adapts to the respective skin environment so that the ecology of these regions of the body is not unbalanced by excessive settlement by microorganisms. Compared with the normal state of the skin, the number of microorganisms decreases in the case of dry skin, while the number of microorganisms increases in the case of moist skin, e.g. as a result of inflammatory changes in the case of eczema, by up to 1000-fold.

Being the barrier layer and surface of the human body, the skin is exposed to a large number of external stress factors. The human skin is an organ which, having diverse specialized cell types—keratinocytes, melanocytes, Langerhans cells, Merkel cells and intercalated sensory cells—protects the body against external influences. A differentiation should be made here between external physical, chemical, and biological influences on the human skin. External physical influences include thermal and mechanical influences, and the effect of radiation. External chemical influences are, in particular, the effect of toxins and allergens. External biological influences include the effect of foreign organisms and the metabolic products thereof.

The surface of the human skin is covered by a fatty film which, depending on the given ratios, is to be considered as an oil-in-water or a water-in-oil emulsion and contains numerous active ingredients, such as e.g. enzymes and vitamins, e.g. vitamin D. This fatty film, which has been formed from the lipids released from the sebaceous glands and keratinocytes, preserves the moisture of the skin and protects the body as a skin barrier against unfavorable environmental factors. This sensitive equilibrium of the skin barrier is disturbed by external or internal factors.

The microorganisms of human skin are subjected to various stress factors. For example, they can be damaged by drying out or by high salt concentrations on the surface of the skin, e.g. after perspiring, which can lead to damage of the skin barrier. However, some of these microorganisms—Staphylococci, Micrococci, Corynebacteria and Brevibacteria—usually have the ability to form compatible solutes in order to protect against drying out or high salt concentration and thus contribute to the formation of an intact skin barrier. The compatible solutes, which are also referred to as stress protection substances, are low molecular weights of substances in cytoplasm.

Hitherto, it has, for example, been attempted to effect care or protection of human skin by hydrophilic substances which themselves bind water (E. A. Galinski, Experientia 49 (1993) 487–496). However, these hydrophilic substances bind water molecules of the water of hydration as well as free water molecules. Although this leads to a binding of water molecules, it does not lead, for example, to a protection of the hydration sheaths of cells, proteins and cell membranes.

The object was therefore to provide cosmetic formulations, the use of which overcome [sic] or at least reduce [sic] the abovementioned skin problems and in particular are [sic] suitable.

for protecting human skin against stress factors, in particular against dryness as a result of high temperatures or very low temperatures at low atmospheric humidity and/or against high salt concentration on the skin, for protecting cells, proteins and/or biomembranes of the human skin, for protecting the microflora of the human skin, and/or for stabilizing the skin barrier.

Surprisingly, we have now found that this object is achieved by the use of one or more compounds chosen from compounds of the formulae Ia and Ib -continued Ib the physiologically compatible salts of the compounds of the formulae Ia and Ib, and the stereoisomeric forms of the compounds of the formulae Ia and Ib, where R is H or alkyl, $R^2$ is H, COOH, COO-alkyl or CO—NH—$R^5$, $R^3$ and $R^4$ are in each case independently of one another H or OH, n is 1, 2 or 3, alkyl is an alkyl radical having 1 to 4 carbon atoms, and $R^5$ is H, alkyl, an amino acid radical, dipeptide radical or tripeptide radical in cosmetic formulations.

Within the scope of the present invention, all compounds above and below chosen from the compounds of the formulae Ia and Ib, the physiologically compatible salts of the compounds of formulae Ia and Ib, and the stereoisomeric forms of the compounds of the formulae Ia and Ib are referred to as "ectoin or ectoin derivatives".

Ectoin-containing cosmetic formulations protect cells, protein, enzymes, vitamins, DNA, cell membranes and biomembranes of the skin against damage as a result of drying out and the withdrawal of water. The hydration effect of ectoin stabilizes the water equilibrium of the Stratum corneum and the skin barrier. Ectoin prevents dry and flaky skin.

In addition, ectoin-containing cosmetic formulations protect the microflora of the skin, which is important for an intact skin barrier, against stress as a result of drying out and high ion concentration after perspiring. The stabilization of the resident skin flora by ectoin or its derivatives is an important prerequisite for the equilibrium of the microenvironment of the skin and the formation of an intact skin barrier.

Ectoin and the ectoin derivatives are low molecular weight cyclic amino acid derivatives which can be obtained from various halophilic microorganisms. Both ectoin and hydroxyectoin have the advantage that they do not react with the cell metabolism.

DE 43 42 560 describes the use of ectoin and ectoin derivatives as moisture-donors in cosmetic products.

The compounds chosen from the compounds of the formulae Ia and Ib, the physiologically compatible salts of the compounds of the formulae Ia and Ib and the stereoisomeric forms of the compounds of the formulae Ia and Ib can be present in the cosmetic preparations as optical isomers, diastereomers, racemates, zwitterions, cations or as a mixture of these. Of the compounds chosen from the compounds of the formulae Ia and Ib, the physiological compatible salts of the compounds of the formulae Ia and Ib and the stereoisomeric forms of the compounds of the formulae Ia and Ib, preference is given to those in which $R^1$ is H or $CH_3$, $R^2$ is H or COOH, $R^3$ and $R^4$ in each case independently of one another are H or OH and n is 2. Of the compounds chosen from the compounds of the formulae Ia and Ib, the physiologically compatible salts of the compounds of the formulae Ia and Ib and the stereoisomeric forms of the compounds of the formulae Ia and Ib, particular preference is given to the compounds (S)-1,4,5,6-tetrahydro-2-methyl-4-pyrimidecarboxylic acid (ectoin) and (S,S)-1,4,5,6-tetrahydro-5-hydroxy-2-methyl-4-pyrimidinecarboxylic acid (hydroxyectoin).

The term "amino acid" means the stereoisomeric forms, e.g. D and L forms, the following compounds: alanine, β-alanine, arginine, asparagine, aspartic acid, cysteine, glutamine, glutamic acid, glycine, histidine, isoleucine, leucine, lysine, methionine, phenylaianine, serine, threonine, tryptophan, tyrosine, valine, γ-aminobutyrate, Nε-acetyllysine, Nδ-acetylornithine, Nγ-acetyldiaminobutyrate and Nα-acetyldiaminobutyrate. L-amino acids are preferred.

Amino acid radicals are derived from the corresponding amino acids.

The radicals of the following amino acids are preferred: alanine, β-alanine, asparagine, aspartic acid, glutamine, glutamic acid, glycine, serine, threonine, valine, γ-aminobutyrate, Nε-acetyllysine, Nδ-acetylornithine, Nγ-acetyldiaminobutyrate and Nα-acetyldiaminobutyrate.

The di- and tripeptide radicals are acid amides according to their chemical nature and decompose upon hydrolysis into 2 or 3 amino acids. The amino acids in the di- and tripeptide radicals are bonded together by amide bonds. Preferred di- and tripeptide radicals are built up from the preferred amino acids.

The alkyl groups include the methyl group $CH_3$, the ethyl group $C_2H_5$, the propyl groups $CH_2CH_2CH_3$ and $CH(CH_3)_2$ and the butyl groups $CH_2CH_2CH_2CH_3$, $H_3CCHCH_2CH_3$, $CH_2CH(CH_3)_2$ and $C(CH_3)_3$. The preferred alkyl group is the methyl group.

Preferred physiologically compatible salts of the compounds of the formulae Ia and Ib are, for example, alkali metal, alkaline earth metal or ammonium salts, such as Na, K, Mg or Ca salts, and salts derived from the organic bases triethylamine or tris(2-hydroxyethyl)amine. Further preferred physiologically compatible salts of the compounds of the formulae Ia and Ib arise by reaction with inorganic acids, such as hydrochloric acid, sulfuric acid and phosphoric acid, or with organic carboxylic or sulfonic acids, such as acetic acid, citric acid, benzoic acid, maleic acid, fumaric acid, tartaric acid and p-toluenesulfonic acid.

Compounds of the formulae Ia and Ib in which basic and acidic groups such as carboxyl or amino groups are present in equal number form internal salts.

The preparation of the compounds of the formula [sic] Ia and Ib is described in the literature (DE 43 42 560). (S)-1,4,5,6-tetrahydro-2-methyl-4-pyrimidinecarboxylic acid or (S,S)-1,4,5,6-tetrahydro-5-hydroxy-2-methyl-4-pyrimidinecarboxylic acid can also be obtained microbiologically (Severin et al., J. Gen. Microb. 138 (1992) 1629–1638).

The cosmetic formulation is prepared by converting one or more compounds chosen from the compounds of the formulae Ia and Ib, the physiologically compatible salts of the compounds of the formulae Ia and Ib and the stereoisomeric forms of the compounds of the formulae Ia and Ib optionally with auxiliaries and/or carriers into a suitable formulation form. The auxiliaries and carriers originate from the group of carriers, preservatives and other customary auxiliaries.

The cosmetic formulations based on one or more compounds chosen from the compounds of the formulae Ia and Ib, the physiologically compatible salts of the compounds of the formulae Ia and Ib and the stereoisomeric forms of the compounds of the formulae Ia and Ib are applied externally. Examples of application forms which may be mentioned are: solutions, suspensions, emulsions, pastes, ointments, gels, creams, lotions, powders, soaps, surfactant-containing cleansing preparations, oils and sprays. In addition to one or more compounds chosen from the compounds of the formulae Ia and Ib, the physiologically compatible salts of the compounds of the formulae Ia and Ib and the stereoisomeric forms of the compounds of the formulae Ia and Ib, any customary carriers, auxiliaries and optionally further active ingredients are added to the formulation.

Preferred auxiliaries originate from the group of preservatives, antioxidants, stabilizers, solubility promoters, vitamins, colorants, odor improvers.

In addition to one or more compounds chosen from the compounds of the formulae Ia and Ib, the physiologically compatible salts of the compounds of the formulae Ia and Ib and the stereoisomeric forms of the compounds of the formulae Ia and Ib, ointments, pastes, creams and gels can comprise the customary carriers, e.g. animal and vegetable fats, waxes, paraffins, starch, tragacanth, cellulose derivatives, polyethylene glycols, silicones, bentonites, silica, talc and zinc oxide or mixtures of these substances.

In addition to one or more compounds chosen from the compounds of the formulae Ia and Ib, the physiologically compatible salts of the compounds of the formulae Ia and Ib and the stereoisomeric forms of the compounds of the formulae Ia and Ib, powders and sprays can comprise the customary carriers, e.g. lactose, talc, silica, aluminum hydroxide, calcium silicate and polyamide powder or mixtures of these substances. Sprays can additionally comprise the customary propellants, e.g. chlorofluorocarbons, propane/butane or dimethyl ether.

In addition to one or more compounds chosen from the compounds of the formulae Ia and Ib, the physiologically compatible salts of the compounds of the formulae Ia and Ib and the stereoisomeric forms of the compounds of the formulae Ia and Ib, solutions and emulsions can comprise the customary carriers, such as solvents, solubility promoters and emulsifiers, e.g. water, ethanol, isopropanol, ethyl carbonate, ethyl acetate, benzyl alcohol, benzyl benzoate, propylene glycol, 1,3-diethylene glycol butyl ether, oils, in particular cottonseed oil, groundnut oil, wheatgerm oil, olive oil, castor oil and sesame oil, glycerol fatty acid esters, polyethylene glycols and fatty acid esters of sorbitan or mixtures of these substances.

In addition to one or more compounds chosen from the compounds of the formulae Ia and Ib, the physiologically compatible salts of the compounds of the formulae Ia and Ib and the stereoisomeric forms of the compounds of the formulae Ia and Ib, suspensions can comprise the customary carriers, such as liquid diluents, e.g. water, ethanol or propylene glycol, suspending agents, e.g. ethoxylated isostearyl alcohols, polyoxyethylene sorbitol esters and polyoxyethylene sorbitan esters, microcrystaline cellulose, aluminum metahydroxide, bentonite, agar agar and tragacanth or mixtures of these substances.

In addition to one or more compounds chosen from the compounds of the formulae Ia and Ib, the physiologically compatible salts of the compounds of the formulae Ia and Ib and the stereoisomeric forms of the compounds of the formulae Ia and Ib, soaps can comprise the customary carriers, such as alkali metal salts of fatty acids, salts of fatty acid half-esters, fatty acid protein hydrolyzates, isothionates [sic], lanolin, fatty alcohol, vegetable oils, plant extracts, glycerol, sugars or mixtures of these substances.

In addition to one or more compounds chosen from the compounds of the formulae Ia and Ib, the physiologically compatible salts of the compounds of the formulae Ia and Ib and the stereoisomeric forms of the compounds of the formulae Ia and Ib, surfactant-containing cleaning products can comprise the customary carrier substances, such as salts of fatty alcohol sulfates, fatty alcohol ether sulfates, sulfosuccinic half-esters, fatty acid protein hydrolyzates, isothionates [sic], imidazolinium derivatives, methyltaurates, sarcosinates, fatty acid amide ether sulfates, alkylamidobetaines, fatty alcohols, fatty acid glycerides, fatty acid diethanolamides, vegetable and synthetic oils, lanolin derivatives, ethoxylated glycerol fatty acid esters or mixtures of these substances.

In addition to one or more compounds chosen from the compounds of the formulae Ia and Ib, the physiologically compatible salts of the compounds of the formulae Ia and Ib and the stereoisomeric forms of the compounds of the formulae Ia and Ib, face and body oils can comprise the customary carrier substances such as synthetic oils, such as fatty acid esters, fatty alcohols, silicone oils, natural oils, such as plant oils and oily plant extracts, paraffin oils, lanolin oils or mixtures of these substances.

Further typically cosmetic application forms are also lipstick, lipcare sticks, mascara, eyeliner, eyeshadows, blusher, powder, emulsion and wax foundation, and sunscreen, presun and aftersun preparations.

The proportion of the compounds chosen from the compounds of the formulae Ia and Ib, the physiologically compatible salts of the compounds of the formulae Ia and Ib and the stereoisomeric forms of the compounds of the formulae Ia and Ib in the cosmetic formulation is preferably from 0.0001 to 50% by weight, particularly preferably from 0.001 to 10% by weight, based on the total cosmetic formulation.

Protection of the skin against drying out can be demonstrated, for example, in vivo, e.g. by known detection methods such as TEWL (tansepidermal water loss), corneometry (to determine the moisture in the skin), microtopography (to determine the roughness of the skin) or SELS (surface elevation of living skin).

Ectoin-containing formulations can, for example, protect the skin barrier against the harmful effect of sodium dodecyl sulfate (SDS). The use of a cosmetic ectoin-containing emulsion can significantly reduce the transepidermal water loss e.g. by up to 40% (FIG. 1) Skin pretreated with an ectoin-containing cosmetic formulation is insensitive toward damage of the skin barrier by the surfactant (SDS). As a result of the use of an ectoin-containing emulsion, the skin is better protected against surfactant damage of the skin and the water loss associated therewith.

An important aim of cosmetics continues to be protection of the skin against stress factors which lead to the drying out of the skin. In particular, dry air during cold or very warm weather conditions leads to a severe loss of water from the skin. Ectoin protects e.g. from a cosmetic O/W emulsion, against drying out (FIG. 2). In addition to the protection against drying out, ectoin-containing cosmetic formulations lead to skin moisture which is significantly better than a corresponding base formulation without ectoin (placebo) but which still comprises 3% glycerol. Furthermore, ectoin-containing cosmetic formulations still effect significantly higher skin moisture compared with the untreated area of skin or areas of skin treated only with the placebo even after 24 hours. Ectoin-containing cosmetic formulations protect the skin against rapid drying out, even against strongly hygroscopic silica gel which is applied directly to the skin. The moisture of the skin can be protected against drying out by the topical application of ectoin-containing cosmetic formulations over an extended period. Ectoin-containing cosmetic formulations are therefore highly suitable for prophylaxis against dry skin.

Stabilization of the biomembranes can be demonstrated e.g. in vitro. Here, use is made of the fact that propidium iodide is not taken up into the cells if the membrane of the skin cells is intact, and dead cells or cells with a damaged membrane are permeable to propidium iodide and are subject to a red coloration as a result of the absorption of propidium iodide.

By comparing cell cultures which have been pretreated with ectoin prior to damage, for example by the addition of DMS0, and cells which have not been pretreated, it is possible to ascertain, following subsequent propidium iodide treatment, the effect of the ectoin or its derivatives on the stabilization of the biomembranes.

To determine the cell membrane- and protein-damaging action of surfactants, the RBC Test can, for example, be used. For this, the erythrocytes are incubated e.g. with sodium dodecyl sulfate (SDS), for example for a period of 10 minutes. SDS destabilizes the membrane of untreated cells such that the cells are partially lysed and their contents such as the hemoglobin are released. The hemoglobin released during cell-wall damage serves as an indicator for the spectrophotometric determination of the membrane damage by SDS. By reference to the hemoglobin released, it is possible to determine the number of destroyed erythrocytes.

Figure 3:
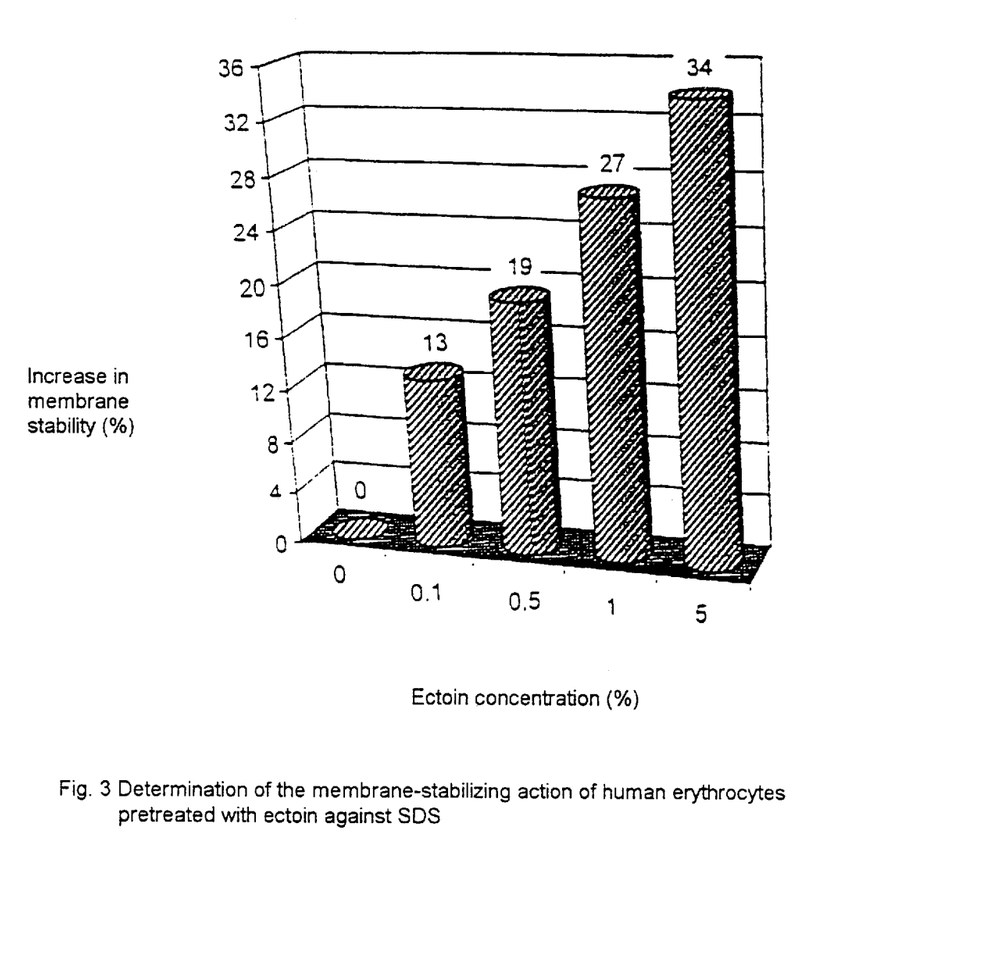

Ectoin protects the cells against damage by SDS (FIG. 3). The erythrocytes pretreated with ectoin are ore resistant toward membrane damage by SDS than untreated cells. The higher the ectoin concentration, the greater the protective effect against membrane damage.

Figure 4:
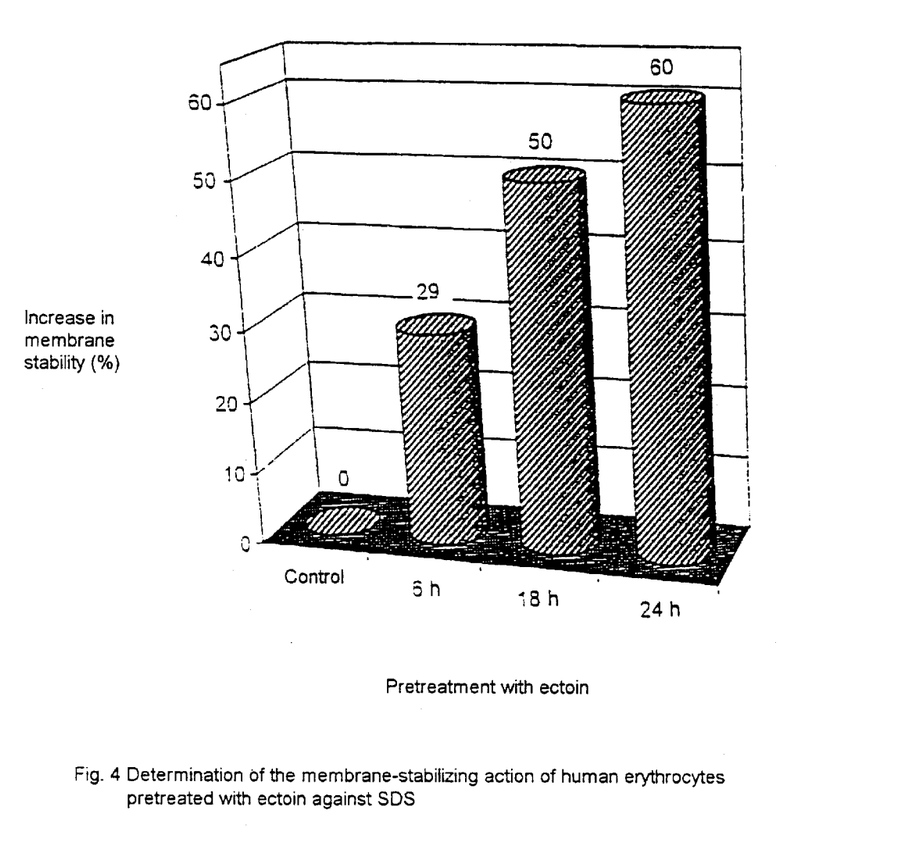

The longer the cells are pretreated with ectoin, the greater the protective effect against membrane damage (FIG. 4). Stabilization of the cell membranes is both dependent on the ectoin concentration and on the duration of ectoin pretreatment. The higher the ectoin concentration and the longer the contact time on the erythrocytes, the greater the cell membranes are protected.

Stabilization of the resident microflora can, for example, be demonstrated in vivo. Following ectoin treatment of certain areas of skin, for example the forearms, the skin is subjected e.g. to dry and/or heat stress in a climatically controlled chamber. The bacteria from the forearms are then isolated, and a "living cell count determination" is carried out using vital staining and a growth curve for determining the kinetics, for example by plating out the bacteria on culture plates (plate method) or by the impedance method using conductivity measurements. A comparison of these results with those for areas of skin not pretreated provides evidence of the effect of ectoin or its derivatives on the stabilization of the resident microflora.

All compounds or components which can be used in cosmetic formulations are either known and available commercially or can be synthesized by known methods.

The examples below serve to illustrate the invention and are in no way to be regarded as a limitation. All percentages are percentages by weight.

The INCI names of raw materials used are as follows (the INCI names are by definition given in English):

| Raw material | INCI name |
| --- | --- |
| Almond oil | Sweet Almond Oil (Prunus Dulcis) |
| Eutanol G | Octyldodecanol |
| Luvitol EHO | Cetearyl Octanoate |
| Oxynex K liquid | PEG-8, Tocopherol, Ascorbyl Palmitate, Ascorbic Acid, Citric Acid |
| Panthenol | Panthenol |
| Karion F liquid | Sorbitol |
| Sepigel 305 | Polyacrylamide, C13–14 Isoparaffin, Laureth-7 |
| Paraffin, low-viscosity | Mineral Oil (Paraffinium Liquidum) |
| Mirasil CM 5 | Cyclomethicone |
| Arlacel 165 | Glyceryl Stearate, PEG-100 Stearate |
| Germaben II | Propylene Glycol, Diazolidinyl urea, Methylparaben, Propylparaben |
| Bianca perfume | Parfum [sic] |
| Abil WE 09 | Polyglyceryl-4 Isostearate, Cetyl Dimethicone Copolyol, Hexyl Laurate |
| Jojoba oil | Jojoba Oil (Buxus Chinensis) |
| Cetiol V | Decyl Oleate |
| Prisorine IPIS 2021 | Isopropyl Isostearate |
| Castor oil | Castor Oil (Ricinus Communis) |
| Lunacera M | Cera Microcristallina |
| Miglyol 812 neutral oil | Caprylic/Capric Triglyceride |

-continued

| Raw material | INCI name |
| --- | --- |
| Eusolex T-2000 | Titanium Dioxide, Alumina, Simethicone |

EXAMPLE 1

The following components are used to prepare a skincare gel (O/W) according to the invention comprising ectoin:

| | | | | % by wt. |
| --- | --- | --- | --- | --- |
| A | Almond oil | | (2) | 8.0 |
| | Eutanol G | | (3) | 2.0 |
| | Luvitol EHO | | (4) | 6.0 |
| | Oxynex K liquid | (Art. No. 108324) | (1) | 0.05 |
| B | Panthenol | (Art. No. 501375) | (1) | 0.5 |
| | Carion F liquid | (Art. No. 102993) | (1) | 4.0 |
| | Preservative | | | q.s. |
| | Water, demineralized | | | ad 100 |
| C | Sepigel 305 | | (5) | 3.0 |
| D | Ectoin | | (1) | 1.0 |

Preservatives which may be used are
  0.05% of propyl 4-hydroxybenzoate (Art. No. 107427) or
  0.15% of methyl 4-hydroxybenzoate (Art. No. 106757)
Preparation:

The combined phase B is introduced slowly into phase C with stirring. The predissolved phase A is then added. The mixture is stirred until the phases are mixed homogeneously. Phase D is then added and stirred until homogeneous.
Sources of supply:
  (1) Merck KGaA, Darmstadt
  (2) Gustav Heess, Stuttgart
  (3) Henkel KGaA, Düsseldorf
  (4) BASF AG, Ludwigshafen
  (5) Seppic, France

EXAMPLE 2

The following components are used to prepare a skincare cream (O/W) according to the invention comprising ectoin:

| | | | | % by wt. |
| --- | --- | --- | --- | --- |
| A | Paraffin, low-viscosity | (Art. No. 107174) | (1) | 8.0 |
| | Isopropyl myristate | (Art. No. 822102) | (1) | 4.0 |
| | Mirasil CM 5 | | (2) | 3.0 |
| | Stearic acid | | (1) | 3.0 |
| | Arlacel 165 | | (3) | 5.0 |
| B | Glycerol, 87% | (Art. No. 104091) | (1) | 3.0 |
| | Germaben II | | (4) | 0.5 |
| | Water, demineralized | | | ad 100 |
| C | Bianca perfume | | (5) | 0.3 |
| D | Ectoin | | (1) | 1.0 |

Preparation:

Firstly, phases A and B are heated separately to 75° C. Phase A is then added slowly to phase B and stirred until a homogeneous mixture forms. Following homogenization of the emulsion, it is cooled to 30° C. with stirring, phases C and D are added, and the mixture is stirred until homogeneous.

Sources of supply:
(1) Merck KGaA, Darmstadt
(2) Rhodia
(3) ICI
(4) ISP
(5) Dragoco

EXAMPLE 3

The following components are used to prepare a sunscreen lotion (W/O) according to the invention comprising ectoin:

|   |   |   |   | % by wt. |
|---|---|---|---|---|
| A | Abil WE 09 |  | (2) | 5.0 |
|   | Jojoba oil |  | (3) | 6.0 |
|   | Cetiol V |  | (4) | 6.0 |
|   | Prisorine 2021 |  | (5) | 4.5 |
|   | Castor oil |  | (6) | 1.0 |
|   | Lunacera M |  | (7) | 1.8 |
|   | Miglyol 812 neutral oil |  | (8) | 4.5 |
| B | Eusolex T-2000 | (Art. No. 105373) | (1) | 3.0 |
|   | Glycerol, 87% | (Art. No. 104091) | (1) | 2.0 |
|   | Sodium chloride | (Art. No. 106400) | (1) | 0.4 |
|   | Preservative |  |  | q.s. |
|   | Water, demineralized |  |  | ad 100 |
| C | Perfume |  | (5) | 0.3 |
| D | Ectoin |  | (1) | 1.0 |

Preservatives which may be used are
0.05% of propyl 4-hydroxybenzoate (Art. No. 107427) or
0.15% of methyl 4-hydroxybenzoate (Art. No. 106757)

Preparation:

Firstly, Eusolex T-2000 is stirred into phase B and heated to 80° C. Phase A is then heated to 75° C. and phase B is slowly added with stirring. The mixture is then stirred until homogeneous and then cooled to 30° C. with stirring. Phases C and D are then added and the mixture is stirred until homogeneous.

Sources of supply:
(1) Merck KGaA, Darmstadt
(2) Th. Goldschmidt AG, Essen
(3) H. Lamotte, Bremen
(4) Henkel KGaA, Düsseldorf
(5) Unichema, Emmerich
(6) Gustav Heess, Stuttgart
(7) H. B. Fuller, Lüneburg
(8) Huls Troisdorf AG, Witten

EXAMPLE 4

The following components are used to prepare a skincare cream (O/W) comprising ectoin:

|   |   |   |   | % by wt. |
|---|---|---|---|---|
| A | Paraffin, low-viscosity | (Art. No. 107174) | (1) | 8.0 |
|   | Isopropyl myristate | (Art. No. 822102) | (1) | 4.0 |
|   | Mirasil CM 5 |  | (2) | 3.0 |
|   | Stearic acid |  | (1) | 3.0 |
|   | Arlacel 165 V |  | (3) | 5.0 |
| B | Glycerol, 87% | (Art. No. 104091) | (1) | 3.0 |
|   | Germaben II |  | (4) | 0.5 |
|   | Water, demineralized |  |  | ad 100 |
| D | Ectoin |  | (1) | X | x=0 (placebo), 2.5% by weight

Preparation:

Firstly, phases A and B are heated separately to 75° C. Phase A is then added slowly to phase B with stirring and stirred until a homogeneous mixture forms. Following homogenization of the emulsion, it is cooled to 30° C. with stirring, phase D is added and the mixture is stirred until homogeneous.

Sources of supply:
(1) Merck KGaA, Darmstadt
(2) Rhodia
(3) ICI
(4) ISP

EXAMPLE 4a

Using the skincare creams (O/W) comprising ectoin described in. Example 4, an in vivo determination of the transepidermal water loss (TEWL) following damage to the skin barrier by SDS treatment is carried out. Firstly, the skin of the subjects (N=5) on the forearm is treated for one week twice daily with the O/W emulsion (2 mg/cm$^2$) comprising 2% and 5% of ectoin and an emulsion without ectoin (placebo). In order to increase the TEWL artificially as a result of damage to the horny barrier, the skin is then treated with 80 μl of sodium dodecyl sulfate (SDS; 2% in water) in an aluminum chamber with occlusion for 24 h. The TEWL determination is carried out in a climatically controlled room at 22° C. and an atmospheric humidity of 60% using a TM210 TEWA meter. FIG. 1 shows the TEWL before and after treatment with the ectoin-containing emulsions, and following damage to the skin barrier by SDS. The values for FIG. 1 are given in Tab. 1.

TABLE 1

In vivo determination of the transepidermal water loss (TEWL) following damage to the skin barrier by SDS treatment

|  | TEWL [g/m$^2$/h] | | |
|---|---|---|---|
|  | Before treatment | After ectoin treatment for 1 week | After SDS stress |
| Untreated | 5.2 | 5.6 | 18 |
| Placebo | 5.2 | 5.8 | 15.1 |
| 2% of ectoin | 5.6 | 5.6 | 14.2 |
| 5% of ectoin | 5.1 | 5.6 | 10.8 |

EXAMPLE 4b

Using the skincare creams (O/W) comprising ectoin described in Example 4, an in vivo determination of the skin moisture following ectoin treatment and dehydration by means of silica gel is carried out. Initially, the skin of the subjects (N=5) is treated on the forearm for one week twice daily with a cosmetic formulation (2 mg/cm$^2$) comprising 2% and 5% of ectoin and a formulation without ectoin (placebo). The moisture content of the skin is determined prior to application and after 1 week four hours after the last application. Silica gel 60 (0.2 g/cm$^2$) is then applied to the test areas of the forearm for two hours with occlusion (dehydration). Following removal of the silica gel, the skin moisture is measured after 10 min, 2 h, 4 h and 24 h in a climatically controlled room at 22° C. and an atmospheric humidity of 60%. The results are shown in FIG. 2.

EXAMPLE 5

Using an aqueous ectoin solution buffered in PBS buffer (22.2 mmol/l of disodium hydrogenphosphate, 5.6 mmol/l of potassium dihydrogenphosphate, 123.3 mmol/l of sodium chloride and 10 mmol/l of glucose), a determination of the membrane-stabilizing action of ectoin pretreated human erythrocytes against SDS is carried out. The RBC test is used here. The percentage membrane stabilization of cells pretreated with ectoin is determined.

Human erythrocytes ($2 \times 10^8$ cells/ml) are treated for 1 hour with 0%, 0.1%, 0.5%, 1% and 5% of ectoin. The cells are then stressed for 10 min with 0 to 0.04% SDS solution. Then, spectrophotometry is used to determine how many cells have been lysed by reference to the free hemoglobin content. FIG. 3 shows the percentage difference of the lysed cells as a function of the ectoin concentration from the pretreatment compared with an untreated control. The experiment is carried out N=5 times.

In addition, human erythrocytes ($2 \times 10^8$ cells/ml) are treated with 1% of ectoin for 0 (control), 6, 18 and 24 hours. The cells are then stressed for 10 min with 0 to 0.04% of SDS solution. Then, spectrophotometry is used to determine how many cells have been lysed by reference to the free hemoglobin content. FIG. 4 shows the percentage difference of the lysed cells as a function of the ectoin concentration from the pretreatment compared with an untreated control. The experiment is carried out N=5 times.

What is claimed is:

1. A method of treating and protecting the skin of a human patient having skin with high sodium dodecyl sulfate concentration, comprising
   a) administering, for a time sufficient to eliminate the sodium dodecyl sulfate concentration, a cosmetic formulation comprising at least one compound of the formulae Ia or Ib Ia Ib or a physiologically compatible salt thereof, or a stereoisomeric form thereof,
   wherein
   $R^1$ is H or alkyl,
   $R^2$ is H, COOH, COO-alkyl or CO—NH—$R^5$,
   $R^3$ and $R^4$ are in each case independently of one another H or OH,
   n is 1, 2 or 3,
   alkyl is an alkyl radical having 1 to 4 carbon atoms, and
   $R^5$ is H, alkyl, or an amino acid radical, dipeptide radical or tripeptide radical and
   b) thereafter continuing to administer the formulation to protect the skin from high sodium dodecyl sulfate concentration.

2. A method according to claim 1, wherein the cosmetic formulation protects cells, proteins and/or biomembranes in the human skin.

3. A method according to claim 1, wherein the cosmetic formulation protects the microflora of the human skin.

4. A method according to claim 1, wherein the cosmetic formulation stabilizes the skin barrier.

5. A method according to claim 1, wherein the cosmetic formulation is an external application formulation in the form of a solution, a suspension, an emulsion, a paste, an ointment, a gel, a cream, a lotion, a powder, a soap, a surfactant-containing cleansing preparation, an oil, a lipstick, a lipcare stick, a mascara, an eyeliner, an eyeshadow, a blusher, a powder, an emulsion or wax foundation, a sunscreen, a presun or aftersun preparation or a spray.

6. A method according to claim 1, wherein the proportion of the compound of formulae Ia or Ib, a physiologically compatible salt thereof, or a stereoisomeric form thereof, is from 0.0001 to 50% by weight, based on the total cosmetic formulation.

7. A method according to claim 1, wherein said compound is (S)-1,4,5,6-tetrahydro-2-methyl-4-pyrimidinecarboxylic acid or (S,S)-1,4,5,6-tetrahydro-5-hydroxy-2-methyl-4-pyrimidinecarboxylic acid.

* * * * *